United States Patent
Braga

(10) Patent No.: US 11,666,491 B2
(45) Date of Patent: Jun. 6, 2023

(54) SURGICAL GAUZE

(71) Applicant: B-RES DI BRAGA ING. GIUSEPPE E C. SAS, Borgosatollo (IT)

(72) Inventor: Carlo Braga, Borgosatollo (IT)

(73) Assignee: B-RES DI BRAGA ING. GIUSEPPE E C. SAS, Borgosatollo (IT)

( * ) Notice: Subject to any disclaimer, the term of this patent is extended or adjusted under 35 U.S.C. 154(b) by 273 days.

(21) Appl. No.: 16/969,303

(22) PCT Filed: Feb. 12, 2019

(86) PCT No.: PCT/EP2019/053449
§ 371 (c)(1),
(2) Date: Aug. 12, 2020

(87) PCT Pub. No.: WO2019/158531
PCT Pub. Date: Aug. 22, 2019

(65) Prior Publication Data
US 2021/0045935 A1 Feb. 18, 2021

(30) Foreign Application Priority Data
Feb. 13, 2018 (IT) .......................... 102018000002612

(51) Int. Cl.
*A61F 13/44* (2006.01)
*A61F 13/36* (2006.01)

(52) U.S. Cl.
CPC .............. *A61F 13/44* (2013.01); *A61F 13/36* (2013.01)

(58) Field of Classification Search
CPC .................................. A61F 13/44; A61F 13/36
See application file for complete search history.

(56) References Cited

U.S. PATENT DOCUMENTS

| 3,698,393 A | 10/1972 | Stone |
| 3,731,685 A | 5/1973 | Eidus |

(Continued)

FOREIGN PATENT DOCUMENTS

| CA | 1114354 A | 12/1981 |
| CA | 2022868 A1 | 2/1991 |

(Continued)

OTHER PUBLICATIONS

Hasan, Mahedi, "Standard Moisture Regain and Moisture Content of Fibers," https://www.textilecalculations.com/standard-moisture-regain-and-moisture-content-of-fibers/, 2015.*

(Continued)

*Primary Examiner* — Susan S Su
*Assistant Examiner* — Eric Rassavong
(74) *Attorney, Agent, or Firm* — Cantor Colburn LLP

(57) ABSTRACT

A surgical gauze includes a single-layer fabric having fibers of at least two groups of fibers. The fibers of the first group of fibers have a higher regain rate than the fibers of the second group of fibers. The fibers of the first group are made of cotton and are white. The fibers of the second group of fibers are made of polymeric material and are blue or green. The first and second groups of fibers identify different regions in the gauze which can be recognized by color with the naked eye before and after use in an operating site. The second group of fibers have a regain rate of less than 1% and weigh less than 10% by weight on the total weight of the surgical gauze.

13 Claims, 2 Drawing Sheets

(56) References Cited

U.S. PATENT DOCUMENTS

| | | | |
|---|---|---|---|
| 4,244,369 A | 1/1981 | McAvinn et al. | |
| 4,910,803 A | 3/1990 | Cukier | |
| 4,917,694 A | 4/1990 | Jessup | |
| 7,465,847 B2 | 12/2008 | Fabian | |
| 2005/0109347 A1 | 5/2005 | Falls et al. | |
| 2008/0030303 A1 | 2/2008 | Kobren et al. | |
| 2011/0151738 A1* | 6/2011 | Moore | D04H 1/435 264/103 |
| 2012/0171276 A1 | 7/2012 | Fujimori et al. | |
| 2013/0035655 A1 | 2/2013 | Nakamura | |
| 2013/0131571 A1 | 5/2013 | Cerra | |
| 2013/0150764 A1 | 6/2013 | Patel et al. | |
| 2016/0247275 A1 | 8/2016 | Chou et al. | |
| 2018/0371689 A1* | 12/2018 | Zimmerman | D06P 5/22 |

FOREIGN PATENT DOCUMENTS

| | | | | |
|---|---|---|---|---|
| CN | 2404504 Y | 11/2000 | | |
| CN | 1911195 A | 2/2007 | | |
| CN | 101843540 A | 9/2010 | | |
| CN | 103857414 A | 6/2014 | | |
| CN | 106413650 * | 11/2014 | | A61F 13/36 |
| CN | 106618871 A | 5/2017 | | |
| CN | 206324922 U | 7/2017 | | |
| EP | 2399559 A1 | 12/2011 | | |
| JP | 2010018920 A | 1/2010 | | |
| WO | 3057783 A1 | 10/2000 | | |
| WO | 2005066406 A1 | 7/2005 | | |
| WO | 2009000426 A1 | 12/2008 | | |
| WO | 2011033540 A1 | 3/2011 | | |
| WO | 2013041976 A1 | 3/2013 | | |
| WO | WO-2013041976 A1 * | 3/2013 | | A61F 13/36 |
| WO | 2015017044 A1 | 2/2015 | | |
| WO | WO-2015017044 A1 * | 2/2015 | | A61B 17/3211 |
| WO | 2015075078 A1 | 5/2015 | | |
| WO | WO-2015075078 A1 * | 5/2015 | | A61F 13/36 |
| WO | WO-2016077259 A1 * | 5/2016 | | A61B 17/06 |

OTHER PUBLICATIONS

Patwary, Mohammad Zillane, "Hemp Fiber | Physical and Chemical Properties of Hemp Fiber," https://textilefashionstudy.com/physical-and-chemical-properties-of-hemp-fiber/, 2012.*

Kiron, Mazharul Islam, "Dyeing of Polyester Faric with Disperse Dyes," https://textilelearner.net/dyeing-of-polyester-fabric-with-disperse-dyes/, 2012.*

International Search Report dated Jun. 17, 2019 re: Application No. PCT/EP2019/053449, pp. 1-6.

IT Search Report dated Oct. 15, 2018 re: Application No. 2018000002612, pp. 1-6.

Written Opinion dated Jun. 17, 2019 re: Application No. PCT/EP2019/053449, pp. 1-9.

* cited by examiner

SURGICAL GAUZE

TECHNICAL FIELD

The present disclosure relates to a surgical gauze.

The term surgical gauze refers to a device, also known as a swab or sponge, used for all types of surgery.

BACKGROUND

Specialized literature data show that the unintentional retention of gauzes, instruments or other material inside the surgery site occurs once every 1000-3000 surgical procedures.

The materials most frequently retained are gauzes and surgical instruments, for example needles, scalpels and forceps.

The main risk factors highlighted in the literature are:
surgery performed in emergency conditions;
unexpected changes of the operating program during surgery;
complexity of the surgery;
fatigue and stress of the surgical team;
situations that facilitate a counting error, for example mutually attached gauzes;
lack of a procedure for the systematic counting of instruments and gauzes;
lack of checking of the integrity of the materials and of the resources at the end of surgical use.

Gauzes impregnated with blood and/or other body liquids substantially assume the same color as the tissues and/or fluids of the patient in the surgical site.

In other words, gauzes "blend in" in the surgical site and are often difficult to identify, particularly when patient bleeding is abundant.

Indeed due to the color change of the gauzes impregnated with the body fluids in the surgical site, the main risk entailed in their use is to forget said gauzes inside the body of the patient.

Retention of gauzes in the human body can easily cause septicemias, infections and pain; in extreme cases, gauze retention can cause the death of the patient even some time after the surgical procedure.

The problem of gauze retention is one of the most strongly felt worldwide.

Gauze counting must be performed in the following steps:
before beginning the surgical procedure (initial count);
during the surgical procedure, before closing a cavity;
upon closing the skin;
at the time of any change of nurse and/or surgeon in charge of the team.

The integrity of the instrument set must be checked in the following steps:
upon opening the sterile package that contains it;
upon passing to the surgeon for use;
upon return from the surgeon after use.

Counting and checking the integrity of the instrument set must be performed by nursing staff (surgical nurse, operating room nurse/support operator) assigned to the counting activity. The surgeon must check the count has been performed and that the total of used and remaining gauzes corresponds to the total of the gauzes received before and during the surgical procedure.

Counting must be performed by speaking out loud.

The counting procedure must be performed by two operators simultaneously (surgical nurse, operating room nurse/support operator).

Upon the initial count of the gauzes, it must be checked that the number provided on the package is exact, by counting individually each gauze and writing the number on the appropriately provided sheet.

All the instruments, gauzes or other material added during the procedure must be immediately counted and recorded in the appropriate documents.

The counting operation must always be documented by signing on the company form "Sheet for preventing retention of gauzes, instruments or other material within the surgical site" to be attached to the paper printout of the operating procedure, which remains stored in the registry of operations.

It is necessary to use containers for the sterile gauzes, used for the surgical procedure, that are differentiated with respect to the containers that contain other gauzes or other operating room material. It is wise to avoid the use of gauzes with radiopaque filament to perform end-of-surgery medications in order to avoid false positives in case of any radiographic control.

If a mismatch in counting or an integrity defect is detected, it is necessary to implement one or more of the actions listed hereafter, until count match is achieved:
recount;
report to the surgeon;
inspection of the operating site;
inspection of the area that surrounds the operating field;
intraoperative x-ray before the patient leaves the operating room;
recording of what has occurred and of the procedures performed in the operating process.

Various technical solutions have been proposed in order to obviate the problem described above.

US-2008/0030303 describes gauzes provided with a colored visible number on their surface in order to facilitate manual counting. This method has been improved by providing the gauzes with labels that can be read by a scanner, for example bar codes.

EP-2399559 describes a method for counting gauzes with a scanner that can be handled by the operator and is connected to an electronic device that displays the counts related to each type of gauze used.

WO-2011/033540 describes a system which comprises gauzes provided with RFID tags, and sensors capable of detecting said tags and transmitting to a computer information related to the presence of the corresponding gauze. Despite the progress made, this solution has not proved itself 100% safe and is insufficient on its own.

U.S. Pat. Nos. 7,465,847, 3,698,393, US-20050109347, WO-2000/057783, US-2013/0035655 and U.S. Pat. No. 4,244,369 describe different solutions based on the presence, on each gauze, of an insert that is x-ray opaque.

At the end of the surgical procedure and before ending the final procedures of the surgery, if the count detects a numeric discrepancy between the introduced gauzes and the removed gauzes, the patient is subjected to an x-ray in order to identify the radiopaque material with which each individual gauze is provided.

Disadvantageously, these known solutions are on average expensive, especially if compared with traditional gauzes, and many hospital facilities in several countries might not equip themselves with these gauzes due to purely economic issues.

U.S. Pat. No. 3,731,685, WO-2013/041976, CA-2022868 describe the use of chemical substances which, applied to the gauze, allow its color shift, i.e., change color, upon the contact with liquids, in particular blood or other organic liquids. The purpose is to maximize the color contrast of the gauze with respect to the tissues of the patient in the surgical site, so as to make the gauze stand out visually and facilitate its identification by the operators.

Disadvantageously, in some circumstances the chemical substances used to impregnate the gauze or the swab can be released into the blood of the surgical site and can color the blood or tissues.

A further drawback is constituted by the fact that once the gauze or swab has changed color, the surgeon is no longer able to discriminate easily the nature of the liquids that are present in the surgical site and are absorbed by the gauze or by the swab itself.

By using chemical reagents on the surface fabric of the gauze, it can become difficult to have a dry fabric that is white, which is optimum in order to distinguish the source of the hemorrhage once it makes contact with body fluids.

Furthermore, the use of reagents sets limitations as regards sterilization methods: for example, sterilization by heat cannot be used when heat-sensitive molecules are involved, and therefore if the gauze turns from white to blue due to the chemical substances contained therein, which react with blood, the surgeon will not be able to distinguish easily a new leak of bile that adds to the bleeding, since bile is green and this color can be noticed on the blue gauze/swab.

The background art proposes further technical solutions.

WO-2009/000426 describes a system for detecting gauzes by means of a microprocessor which generates an acoustic signal if the gauze remains inside the surgical site at the end of the surgery just before closing up the patient.

U.S. Pat. No. 4,910,803 describes a first layer of liquid-repellent fabric.

CA 1114354 describes a first blood-repellent layer.

US-2016/0247275 shows a control system for detecting images of the gauze during a surgical procedure.

US-2013/0131571 describes color patterns of gauzes/bandages that aid location, minimizing the loss of these devices, obviating their infection problems.

WO-2005/066406 and CA-2022868 describe fabrics that are colored in order to facilitate viewing.

Finally, WO-2015075078 describes a multilayer gauze which comprises an impermeable layer comprised between two absorbing layers. Such impermeable layer comprises windows for the passage of body fluid.

SUMMARY

The aim of the present disclosure is to provide a surgical gauze that is capable of improving the background art in one or more of the aspects indicated above.

Within this aim, the disclosure provides a surgical gauze that is extremely easy to identify with the naked eye in the operating site even when it is impregnated with body fluid.

The disclosure also provides a surgical gauze that has a body fluid absorption capacity that is comparable with that of traditional gauzes.

The disclosure further provides a surgical gauze that is highly reliable, relatively easy to provide and at competitive costs.

This aim, as well as these and other advantages which will become better apparent hereinafter, are achieved by providing a surgical gauze according to the independent claims, optionally provided with one or more of the characteristics of the dependent claims.

BRIEF DESCRIPTION OF THE DRAWINGS

Further characteristics and advantages of the disclosure will become better apparent from the description of some preferred but not exclusive embodiments of the surgical gauze according to the disclosure, illustrated by way of non-limiting example in the accompanying drawings, wherein.

DETAILED DESCRIPTION OF THE DRAWINGS

Figure 1:
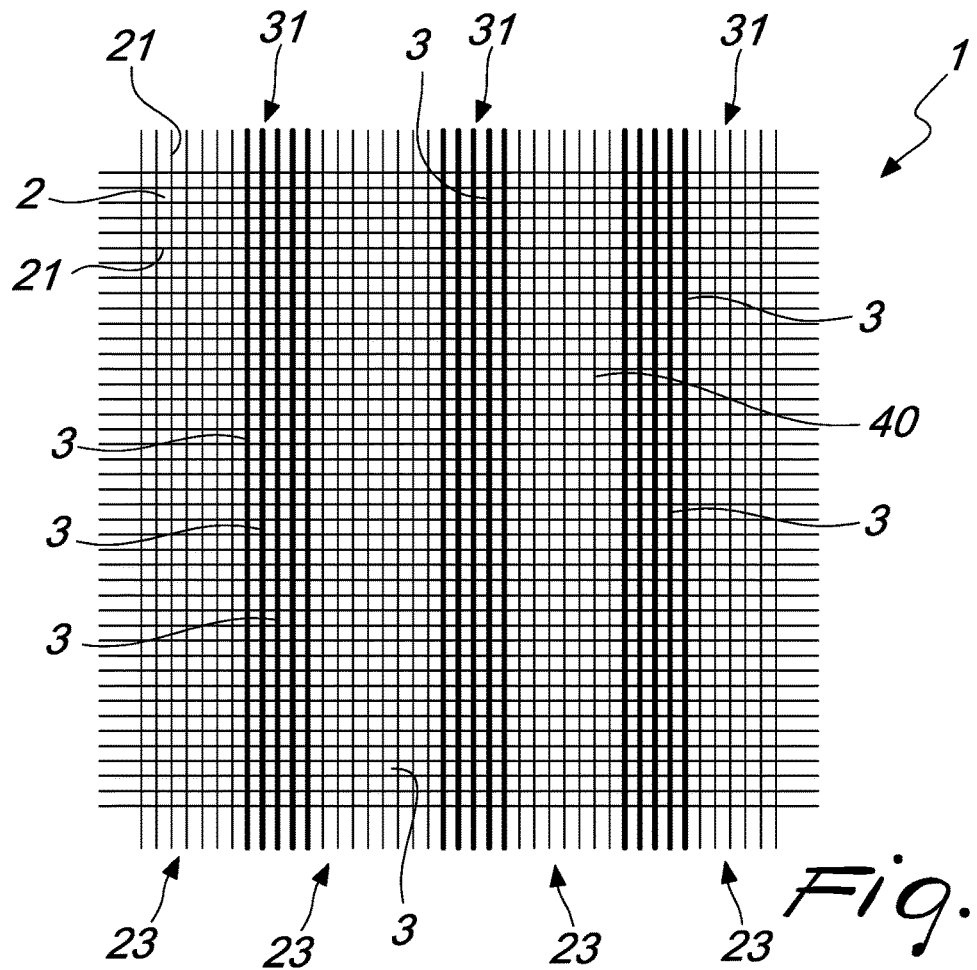
FIG. 1 is a top plan view of a gauze according to a first embodiment of the present disclosure.

With reference to the cited figures, a surgical gauze according to the disclosure, designated generally by the reference numeral 1, comprises a single-layer fabric which comprises fibers of at least one first group of fibers 2 and fibers of at least one second group of fibers.

The single-layer fabric preferably has a weft and warp weaving which comprises fibers (or filaments) of the first group of fibers 2 and fibers (or filaments) of the second group of fibers 3.

FIG. 1 allows to distinguish horizontal filaments 21 and vertical filaments 22.

The surgical gauze 1 comprises portions 23 in which horizontal filaments 21 cross vertical filaments 22.

The fibers of the second group of fibers 3 are vertical.

The vertical filaments/fibers 21, 3 are to be considered warp and the horizontal filaments/fibers 22 are to be considered weft. However, an inverse configuration is possible.

It is known that the weaving of weft and warp forms a fabric.

The fibers of the first group of fibers 2 have a higher regain rate than the fibers of the second group of fibers 3.

The fibers of the first group of fibers 2 are preferably made of cotton, while the fibers of the second group 3 are made of polymeric material.

The fibers of the first group of fibers may also be made of NWF (nonwoven fabric).

The fibers of the first group may also be made at least partially of hemp or hemp waste.

The fibers of the first group of fibers 2 are white and the fibers of the second group of fibers 3 are blue or green.

The first and second groups of fibers (2, 3) identify different regions (23, 31) in the surgical gauze (1) which can be recognized by color with the naked eye before and after use in an operating site.

The second group of fibers 3 has a regain rate of less than 1% and weighs less than 10% by weight on the total weight of the surgical gauze 1.

In this manner, it has been observed that one obtains a surgical gauze 1 that allows an effective identification of the second group of fibers while maintaining an absorption capacity that is comparable with traditional gauzes entirely made of cotton.

The filaments 3 are grouped in portions 31 which, in the present embodiment, are strips.

One or more filaments 22 can be present in said portions 31 between two filaments 3.

The density of the weave defines the breadth of small windows 40 through which the body fluid passes and which allow an albeit minimal visibility.

The term filament refers to threads and yarns and more generally to an element having an elongated shape.

It is known that thread is a set of continuous fibers, held together by S- or Z-twisting depending on the direction of twisting. Generally, threads are made of synthetic or artificial material, except in the case of silk, the only continuous fiber that we find in nature.

Yarn is instead a set of discontinuous fibers, held together by S- or Z-twisting. For example, yarns made of cotton and wool are known.

Synthetic yarns are also known which are constituted by the twisting of a set of continuous fibers cut with a cotton cut (3.5-4.5 cm) or wool cut (2-9 cm).

Synthetic threads are constituted by a set of filaments derived from the extrusion of the synthetic polymer.

The filament constituted by the second group of fibers 3 described in the present embodiment is a polymeric thread and therefore a synthetic thread with a single filament or preferably with multiple filaments in order to facilitate its processing on a loom.

In any case, the filaments 2, 3 are to be considered as formed by fibers. It is known that surgical gauzes can be manufactured by using a perpendicular weft and warp loom (air jet, shuttle, projectile) according to a traditional method or by using a chain loom (Raschel, crochet, . . . ).

The surgical gauze 1 described in the present embodiment is obtained with a perpendicular weft and warp loom.

Preferably, the fibers of the second group of fibers 3 have a regain rate comprised between and including 0.1% and 0.3%.

Advantageously, the fibers of the second group of fibers 3 have a regain rate equal to 0.1%.

The term regain rate is understood to refer to the commercial or conventional regain rate in accordance with Italian law no. 883 dated 26 Nov. 1973 (and subsequent amendments) and with Community Directive 96/74/CE.

It is known that the regain rate is essentially the humidity content that must be added to any textile material in the dry state in order to identify the exact value of commercial mass that must be billed.

The regain rate is expressed in percentage values and law no. 883/1973 comprises a table (Annex B) which lists the regain rates of the main fibers.

The higher the regain rate, the higher the humidity absorption of the fiber.

Regain rates are commonly higher than 1%.

A regain rate of less than 1% is certainly to be considered low.

The regain rate of the fibers of the second group of fibers 3 is, as already mentioned, preferably comprised between 0.1% and 0.3%.

Conveniently, the regain rate of the filament 3 is greater than or equal to 0.1%, so as to maintain an albeit minimal absorption capacity.

In this manner, the filament 3 is not impermeable but is slightly absorbent.

The (inherent) regain rate of the filaments 2 is higher than the inherent regain rate of the filaments 3.

The Applicant has performed a test considering two gauzes measuring 3 cm$^2$ and weighing 0.02 g prior to impregnation, in particular a common cotton gauze and a gauze 1 according to the present disclosure.

After impregnating the two gauzes for 60 seconds with human blood and draining them for 30 seconds, a weight of 0.20 g of the gauze 1 and of 0.22 g of the common cotton gauze was measured.

The gauze 1 therefore maintains substantially the same absorption capacity of a common cotton gauze, since the filaments 3 are in a small percentage on the total weight.

Advantageously, however, the filaments 3, indeed because they do not absorb or in any case absorb only slightly the body fluid, remain clearly visible in the operating site. Under the artificial light of the lamps of the operating room, a true reflective effect is produced and the filaments 3 become almost shiny and clearly visible to the naked eye.

A common blue cotton filament, if impregnated with blood, becomes matt black, while the filament 3 as described above becomes "midnight blue", i.e., a "livelier" and more visible color.

If the filament 3 had a non-low regain rate, it would tend to absorb too much body fluid, thus blending in within the operating site.

A technical advantage in accordance with the present disclosure can be deduced in any case even if the filaments 3 have an inherent regain rate of more than 0.1 but in any case less than 1%.

The filament 3 is a synthetic polymeric fiber, preferably polyester or polyethylene.

These materials have high color fastness and high resistances to contact with acids and bases, ensuring their total stability in all operating conditions and excluding chemical contaminations of the operating site.

It is pointed out that in such table annexed to law no. 883/1973 polyester or polyethylene fibers have a regain rate of 1.5%.

The filament 3 therefore has a much lower regain rate than the reference regain rate of polyester and polyethylene fibers.

The filaments 2 are, as already mentioned, made of cotton, the fiber of which has a regain rate comprised between 8.5% and 10.5%.

The absorbent filaments 2 therefore have a distinctly higher regain rate than the absorbent filaments 3.

It should be noted that after weaving the cotton fiber is whitened with caustic soda (4 g/l) and hydrogen peroxide (12 g/l) for 4 hours in an autoclave at 110° C. This provides the white appearance of known gauzes and increases the regain rate in addition to the absorption rate of the fiber. It must be specified, from a purely technical point of view, that the main object of the treatment is to whiten the fiber and that the regain rate increase is an indirect consequence. The regain rate of the filament 3 (for example polyester) instead remains unchanged. Whitening therefore enhances the difference in regain rate of the filaments 2 with respect to the filaments 3.

The weft and warp association of cotton filaments 2 (or nonwoven fiber) with filaments 3 allows to maximize the functionalities of the surgical gauze 1 in terms of absorption (hemorrhage control) and detectability (recovery or location function).

The quantity of filaments 3 with respect to the filaments 2 depends on cost, absorption and visibility requirements.

The most indicated color for the filament 3 is blue or, as an alternative, green, since in contact with both red or green fluids that are generally present in the operating cavity it maintains its initial colorimetric characteristics, its only change being a slight filling of the tone (it becomes darker).

In FIGS. 1-4, the filaments 3 can be recognized since they are shown with thicker black lines.

Figure 2:
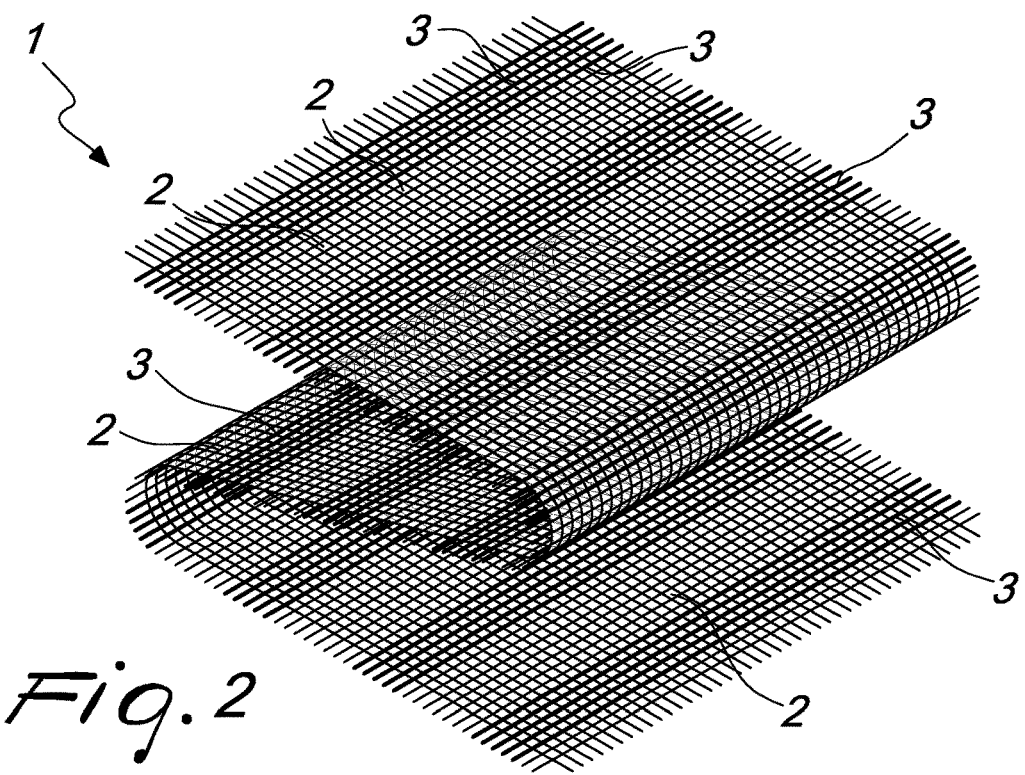
FIG. 2 is a view of the gauze of FIG. 1 in a folded condition.
Figure 3:
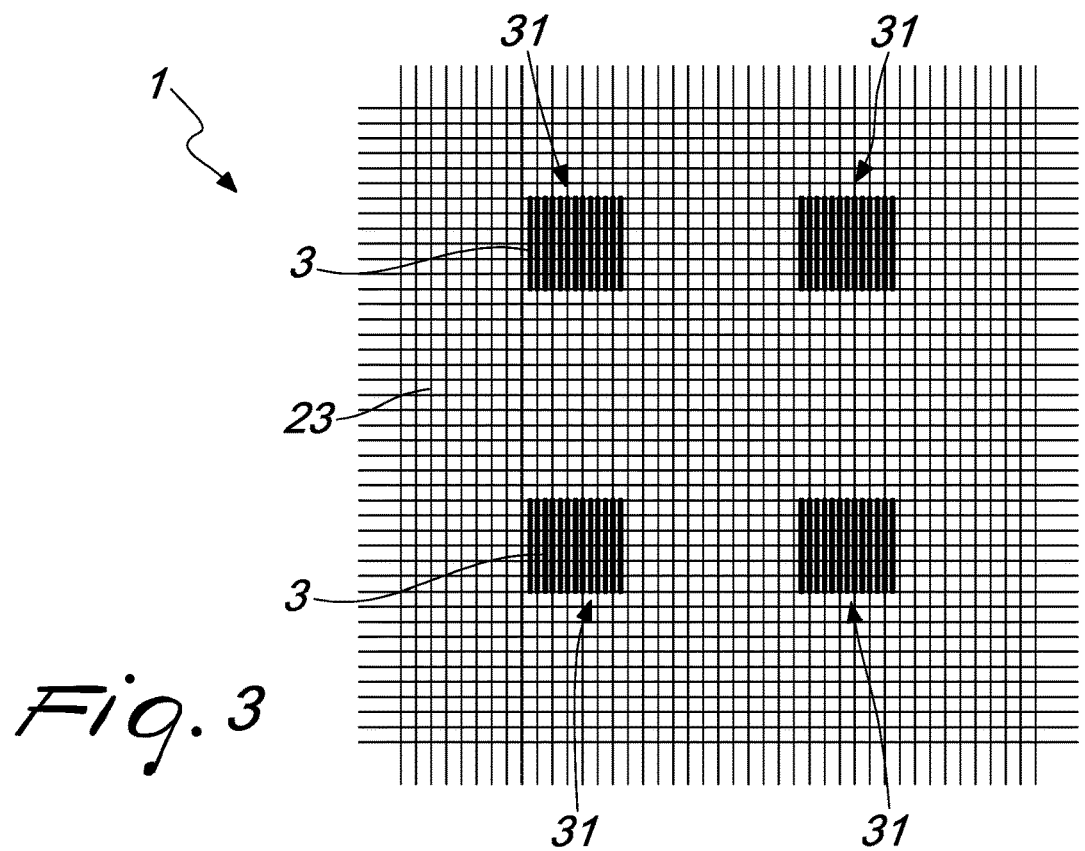
FIG. 3 is a top plan view of a gauze according to a second embodiment of the present disclosure.

The surgical gauze 1 shown in FIGS. 1-2 has long filaments 3: the association with the filaments 2 can also occur in limited regions 32 with grouped shorter filaments 3 (FIG. 3), giving even a checker-like configuration to the gauze 1.

Figure 4:
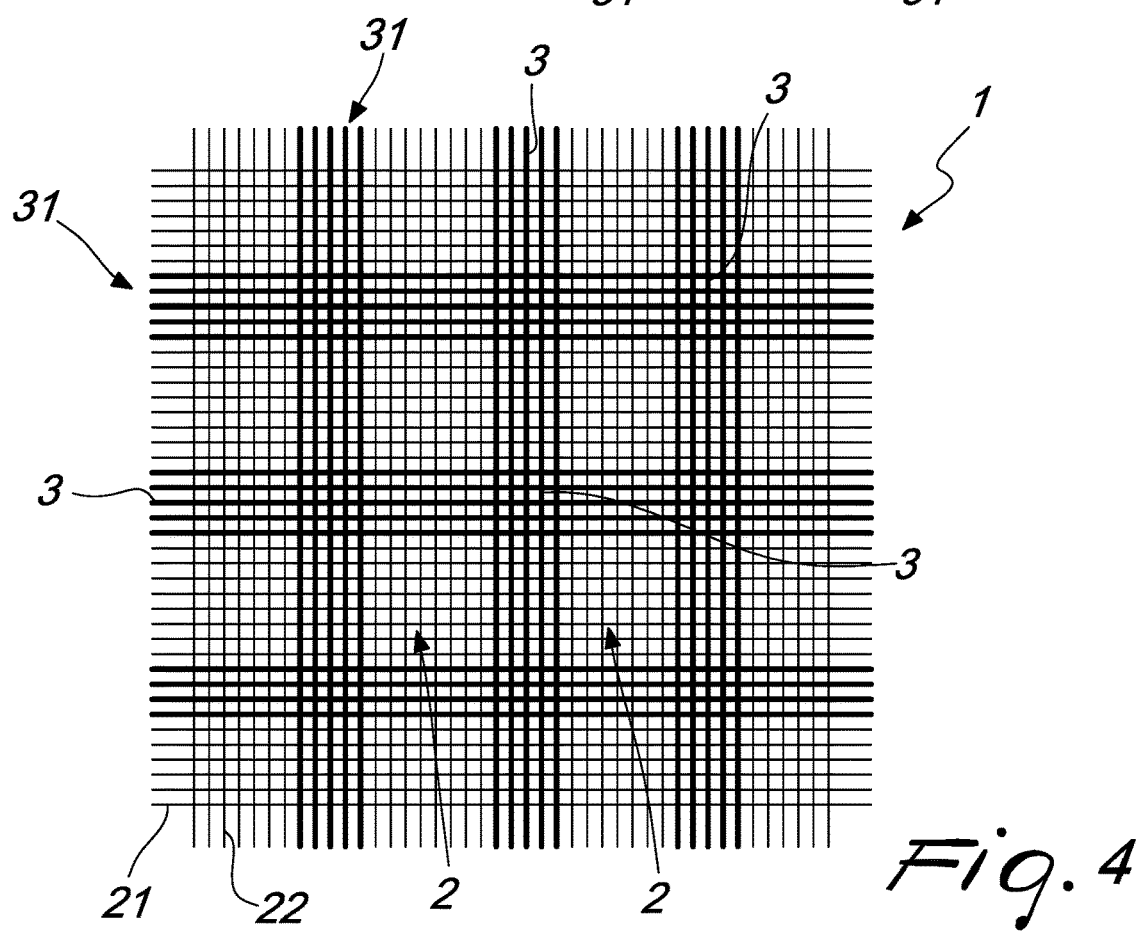
FIG. 4 is a top plan view of a gauze according to a third embodiment of the present disclosure.

As an alternative, it is also possible to provide horizontal (weft) filaments 3, thus forming a crossing of strips of filaments 3 (FIG. 4).

The weft and warp production method improves the economy of manufacture of the gauze 1, which can be produced in several meters and then cut transversely.

Advantageously, the second group of fibers 3 is treated by adding a high energy disperse dye.

Conveniently, the first group of fibers 2 comprises cotton treated by means of a process for increasing its absorption capacity.

According to a preferred practical embodiment, said cotton is treated by means of a staining process with alum.

The fibers of the first group of fibers 2 are associated by means of a covalent bond with molecules of iodine-based or barium-based contrast media.

Advantageously, the surgical gauze 1 comprises a finishing treatment by association with zinc salts.

The processes and/or treatments mentioned above can be provided also independently of each other.

It is noted that both the method for manufacturing the gauze and any additional processes or treatments are absolutely compatible with the current methods for the manufacture of surgical gauzes: this obviously allows to manufacture the gauze according to the disclosure with production costs that are in line with the costs of the gauzes currently in use.

The present disclosure furthermore relates to a method for providing a surgical gauze 1, characterized in that it provides for the weft and warp weaving of fibers that belong to at least one first group of fibers 2 with fibers that belong to at least one second group of fibers 3.

The fibers of the first group of fibers 2 have a higher regain rate than the fibers of the second group of fibers 3.

The fibers of the first group are made of cotton and the fibers of the second group of fibers 3 are made of polymeric material.

The fibers of the first group of fibers 2 may also be made of NWF (nonwoven fabric).

The fibers of the first group of fibers 2 are white and the fibers of the second group of fibers 3 are blue or green.

The first and second groups of fibers (2, 3) identify different regions (23, 31) in the surgical gauze 1 which can be recognized by color with the naked eye before and after use in an operating site.

The second group of fibers has a regain rate of less than 1% and weighs less than 10% by weight on the total weight of the surgical gauze 1.

Advantageously, the method for providing a surgical gauze comprises a step of treating the first group of fibers 2 which is adapted to increase their absorption capacity.

This treatment comprises for example staining with alum.

According to a possible variation of embodiment, the first group of fibers comprises cotton or hemp treated by means of a process for increasing its absorption capacity.

In particular, the surgical gauze 1 comprises a single-layer fabric comprising fibers of at least one first group of fibers 2 and fibers of at least one second group of fibers 3, the fibers of the first group of fibers 2 having a higher regain rate than the fibers of the second group of fibers 3, the fibers of the first group 2 being made at least partially of cotton or hemp and the fibers of the second group being made of polymeric material, the fibers of the first group of fibers 2 being white and the fibers of the second group of fibers 3 being blue or green, the first and second groups of fibers 2, 3 identifying different regions 23, 31 in the gauze 1 which can be recognized by color with the naked eye before and after use in an operating site, the second group of fibers having a regain rate of less than 1%, the first group of fibers comprises cotton or hemp treated by means of a process for increasing its absorption capacity.

Preferably, the cotton or hemp is treated by staining with alum.

In this regard, tests have been conducted on a sample of gauze 1 (only in relation to the portion provided with the first group of fibers 2, made of cotton in the specific case) weighing 0.004 grams.

The samples were tested in the following manner
duration of immersion in water: 1 minute;
duration of shaking and subsequent weighing: 30 seconds.
Two tests were performed for each type of impregnation:
1) Untreated Fabric
0.004 g start-0.038 g after
0.004 g start-0.040 g after
2) 10% Treated Fabric
0.004 g start-0.050 g after
0.004 g start-0.043 g after
3) 20% Treated Fabric
0.004 g start-0.056 g after
0.004 g start-0.055 g after
4) 60% Treated Fabric In this case, the sample had an uneven appearance as regards the cotton and upon handling the fabric the salts were released in the hand.

The results of the test were as follows:
0.004 g start-0.036 g after
0.004 g start-0.035 g after At these higher percentages it is possible to hypothesize in any case an increase in absorbence by associating heat setting.

After impregnation it is possible to subject the impregnated fabric to temperatures around 100° C. (or even higher, for example up to 120° C.) for a time comprised between 5 and 15 minutes, preferably 10 minutes.

This treatment causes higher alum percentages to bind the cotton fiber more.

We can thus estimate that an actual percentage of 60% might bring the cotton from a weight of 0.004 g to a weight, after the same impregnation test and shaking, of 0.080 g.

After heat-setting, if any, the polyester also can be expected to increase its absorption trend, since the alum that does not bind it in a natural manner, following heat-setting, might bind due to a thermal effect while maintaining the chromatic effect of visibility and not so as to confuse the user (surgical team).

Typically, cotton fiber has a regain rate of 8.5; after weaving, the fiber is whitened with caustic soda (4 g/l) and hydrogen peroxide (12 g/l) for 4 hours in an autoclave at 110° C. This provides the white appearance of known gauzes and increases the regain rate, in addition to the absorption rate of the fiber.

We must specify, from a purely technical viewpoint, that the main purpose of the treatment is to whiten the fiber and that the increase of the regain rate is an indirect consequence.

Staining with alum, moreover, makes it possible to obtain further advantages from the hemostatic, antiputrescent, bacteriostatic and astringent point of view.

The use of the surgical gauze 1 according to the disclosure is evident from what has been described above.

The provision of regions constituted by the fibers of the second group of fibers which can be recognized by color with the naked eye before and after use in an operating site allows to identify very rapidly the position of the surgical gauzes with the naked eye.

In practice it has been found that the disclosure achieves the intended aim and advantages.

The disclosure thus conceived is susceptible of numerous modifications and variations, all of which are within the scope of the appended claims; all the details may further be replaced with other technically equivalent elements.

In practice, the materials used, so long as they are compatible with the specific use, as well as the contingent shapes and dimensions, may be any according to the requirements and the state of the art.

The disclosures in Italian Patent Application No. 102018000002612 from which this application claims priority are incorporated herein by reference.

The invention claimed is:

1. A surgical gauze, comprising a single-layer fabric comprising fibers of at least one first group of fibers and fibers of at least one second group of fibers, said fibers of said first group of fibers having a higher regain rate than said fibers of said second group of fibers,
   the fibers of said first group being made of cotton and the fibers of said second group being made of polymeric material,
   the fibers of said first group of fibers being white and the fibers of said second group of fibers being blue or green,
   said first and second groups of fibers identifying different regions in the surgical gauze which can be recognized by color with the naked eye before and after use in an operating site,
   said second group of fibers having a regain rate of less than 1% and weighing less than 10% by weight on the total weight of the surgical gauze.

2. The surgical gauze according to claim 1, wherein said fibers of said second group of fibers have a regain rate comprised between and including 0.1% and 0.3%.

3. The surgical gauze according to claim 1, wherein said fibers of said second group of fibers have a regain rate equal to 0.1%.

4. The surgical gauze according to claim 1, wherein said second group of fibers is treated by adding a high energy disperse dye.

5. The surgical gauze according to claim 1, wherein said first group of fibers comprises cotton treated by a process for increasing absorption capacity.

6. The surgical gauze according to claim 5, wherein said cotton is treated by a staining process with alum.

7. The surgical gauze according to claim 1, wherein said fibers of said first group of fibers are associated by a covalent bond with molecules of iodine-based or barium-based contrast media.

8. The surgical gauze according to claim 1, further comprising a finishing treatment by association with zinc salts.

9. A method for providing a surgical gauze, the method including the following steps:
   providing at least one first group of fibers,
   providing at least one second group of fibers having a lower regain rate than said fibers of said first group of fibers, and
   weft and warp weaving fibers that belong to at least one first group of fibers with fibers that belong to at least one second group of fibers,
   wherein the fibers of said first group are made of cotton and are white and the fibers of said second group are made of polymeric material and are blue or green,
   said first and second groups of fibers identify different regions in the surgical gauze configured to be recognized by color with the naked eye of a user before and after use in an operating site,
   said second group of fibers having a regain rate of less than 1% and weighing less than 10% by weight on the total weight of the surgical gauze.

10. The method for providing a surgical gauze according to claim 9, further including a step of treatment of said first group of fibers which is adapted to increase their absorption capacity.

11. A surgical gauze comprising a single-layer fabric comprising fibers of at least one first group of fibers and fibers of at least one second group of fibers,
   said fibers of said first group of fibers having a higher regain rate than the fibers of said second group of fibers,
   the fibers of said first group being made at least partially of hemp and the fibers of said second group being made of polymeric material,
   said fibers of said first group of fibers being white and the fibers of said second group of fibers being blue or green,
   said first and second groups of fibers identifying different regions in the surgical gauze which can be recognized by color with the naked eye before and after use in an operating site,
   said second group of fibers having a regain rate of less than 1% and weighing less than 10% by weight on the total weight of the surgical gauze.

12. A surgical gauze, comprising a single-layer fabric comprising fibers of at least one first group of fibers and fibers of at least one second group of fibers,
   said fibers of said first group of fibers having a higher regain rate than said fibers of said second group of fibers,
   the fibers of said first group of fibers being made of cotton or hemp and the fibers of said second group of fibers being made of polymeric material,
   said fibers of said first group of fibers being white and the fibers of said second group of fibers being blue or green,
   said first and second groups of fibers identifying different regions in the surgical gauze which can be recognized by color with the naked eye before and after use in an operating site,
   said second group of fibers having a regain rate of less than 1% and weighing less than 10% by weight on the total weight of the surgical gauze,
   said first group of fibers comprises cotton or hemp treated by means of a process for increasing its absorption capacity.

13. The surgical gauze according to claim 12, wherein said cotton or said hemp is treated by staining with alum.

* * * * *